(12) United States Patent
Sainath et al.

(10) Patent No.: US 8,270,562 B2
(45) Date of Patent: Sep. 18, 2012

(54) MULTIPLE X-RAY TUBE SYSTEM AND METHOD OF MAKING SAME

(75) Inventors: Paavana Sainath, Oconomowoc, WI (US); Peter Crandall, Oconomowoc, WI (US); Abdelaziz Ikhlef, Waukesha, WI (US); Chad Smith, Franklin, WI (US); Ron Kent Hockersmith, Waukesha, WI (US); Baojun Li, Sharon, MA (US)

(73) Assignee: General Electric Company, Schenectady, NY (US)

( * ) Notice: Subject to any disclaimer, the term of this patent is extended or adjusted under 35 U.S.C. 154(b) by 79 days.

(21) Appl. No.: 12/642,965

(22) Filed: Dec. 21, 2009

(65) Prior Publication Data

US 2011/0150174 A1  Jun. 23, 2011

(51) Int. Cl.
*A61B 6/00* (2006.01)

(52) U.S. Cl. ............................................ 378/9; 378/124

(58) Field of Classification Search ............... 378/9, 124
See application file for complete search history.

(56) References Cited

U.S. PATENT DOCUMENTS

| 7,187,756 | B2 | 3/2007 | Gohno et al. | |
| 2004/0174946 | A1* | 9/2004 | Hsieh | 378/4 |
| 2005/0226375 | A1* | 10/2005 | Eberhard et al. | 378/62 |

FOREIGN PATENT DOCUMENTS

WO  WO 2008024586 A2 *  2/2008

* cited by examiner

*Primary Examiner* — Hoon Song
*Assistant Examiner* — Mona M Sanei
(74) *Attorney, Agent, or Firm* — Ziolkowski Patent Solutions Group, SC (57) ABSTRACT

An imaging system includes a rotatable gantry having an opening therein to receive a subject to be scanned and configured to rotate about a central axis in a rotation direction. The imaging system also includes a first x-ray source coupled to the rotatable gantry at a first position, wherein the first position is offset from the central axis of the rotatable gantry by a first distance. Further, the imaging system includes a second x-ray source coupled to the rotatable gantry at a second position, wherein the second position is offset from the central axis of the rotatable gantry by a second distance, wherein the second position is offset from the first position in a direction coincident with the rotation direction, and wherein the second position is offset from the first position in a direction parallel to the central axis.

20 Claims, 5 Drawing Sheets

MULTIPLE X-RAY TUBE SYSTEM AND METHOD OF MAKING SAME

BACKGROUND OF THE INVENTION

The invention relates generally to diagnostic imaging and, more particularly, to a multiple x-ray tube system and method of making same.

X-ray systems typically include an x-ray tube, a detector, and a support structure for the x-ray tube and the detector. In operation, an imaging table, on which an object is positioned, is located between the x-ray tube and the detector. The x-ray tube typically emits radiation, such as x-rays, toward the object. The radiation typically passes through the object on the imaging table and impinges on the detector. As radiation passes through the object, internal structures of the object cause spatial variances in the radiation received at the detector. The detector then emits data received, and the system translates the radiation variances into an image, which may be used to evaluate the internal structure of the object. One skilled in the art will recognize that the object may include, but is not limited to, a patient in a medical imaging procedure and an inanimate object as in, for instance, a package in an x-ray scanner or computed tomography (CT) package scanner.

Some applications for x-ray imaging using x-ray tubes include dual kVp operation to enable energy discrimination by using detectors configured to be responsive to different x-ray spectra. For example, a conventional third-generation CT system may acquire x-ray projection data sequentially at different peak kilovoltage (kVp) levels of the x-ray source, which changes the peak and spectrum of energy of the incident photons comprising the emitted x-ray beams. Energy sensitive detectors may be used such that each x-ray photon reaching the detector is recorded with its photon energy. The detected signals from two energy regions provide sufficient information to resolve the energy dependence of the material being imaged. Furthermore, detected signals from the two energy regions provide sufficient information to determine the relative composition of an object composed of two hypothetical materials.

It is generally desirable to have increased speed, coverage, and resolution of CT scanners, for example, to improve imaging of the cardiac region. In recent years, manufacturers have improved scanners by increasing the gantry speed, by reducing the pixel size, and by extending the coverage of the detectors in a z-direction (e.g., axial or along the patient axis of a CT system) by extending the length of the detector in the z-direction. This approach has resulted in development of CT systems that have larger detectors. Detectors, in principle, may be extended in the z-direction to cover the entire cardiac region. However, such a length may be undesirable because, as detectors get longer in the axial (z) direction, an increase in the cone angle occurs as well. The cone angle is the angle, along the z-direction, between the focal spot and the edges of the detector. At small cone angles (i.e., at the center region of the cone), complete data sets are obtained. However, data is incomplete at increased cone angles (i.e., at the outer edges of the cone), which results in unstable reconstruction and leads to cone beam artifacts in reconstructed images.

Cone beam angles may be decreased by emitting x-ray beams from multiple x-ray tubes that are spaced apart from one another along the z-direction. However, properly aligning and calibrating the x-ray tubes along the z-direction adds significant complexity to the manufacturing process and, therefore, increases the cost of the imaging system.

Therefore, it would be desirable to design a system and method that reduces cone beam artifacts while simplifying the manufacturing complexity of the imaging system.

BRIEF DESCRIPTION OF THE INVENTION

Embodiments of the present invention are directed to a multiple x-ray tube system and method of making same.

According to an aspect of the invention, an imaging system includes a rotatable gantry having an opening therein to receive a subject to be scanned and configured to rotate about a central axis in a rotation direction. The imaging system also includes a first x-ray source coupled to the rotatable gantry at a first position, wherein the first position is offset from the central axis of the rotatable gantry by a first distance. Further, the imaging system includes a second x-ray source coupled to the rotatable gantry at a second position, wherein the second position is offset from the central axis of the rotatable gantry by a second distance, wherein the second position is offset from the first position in a direction coincident with the rotation direction, and wherein the second position is offset from the first position in a direction parallel to the central axis.

In accordance with another aspect of the invention, a method of manufacturing an assembly includes coupling a first x-ray tube to a rotatable gantry at a first location, wherein the first location is offset from a center of rotation of the rotatable gantry by a first distance. The method also includes coupling a second x-ray tube to the rotatable gantry at a second location, wherein the second location is offset from the center of rotation of the rotatable gantry by a second distance, offset from the first location in a direction parallel to the center of rotation of the rotatable gantry, and offset from the first location in a direction of rotation of the rotatable gantry.

According to yet another aspect of the invention, a computed tomography (CT) system includes a gantry having an opening therein for receiving an object to be scanned, the gantry rotatable in a circumferential direction. The CT system also includes a table positioned within the opening of the rotatable gantry and moveable through the opening in a z-direction and a first x-ray tube coupled to the rotatable gantry and configured to emit a first stream of electrons, the first x-ray tube having a first focal spot configured to direct a first beam of x-rays toward a detector. The CT system further includes a second x-ray tube configured to emit a second stream of electrons and having a second focal spot configured to direct a second beam of x-ray beam toward the detector, wherein the second focal spot is offset from the first focal spot by a distance in the z-direction and by a distance in the circumferential direction.

Various other features and advantages will be made apparent from the following detailed description and the drawings.

BRIEF DESCRIPTION OF THE DRAWINGS

The drawings illustrate several preferred embodiments presently contemplated for carrying out the invention.

In the drawings.

DETAILED DESCRIPTION

Figure 1:
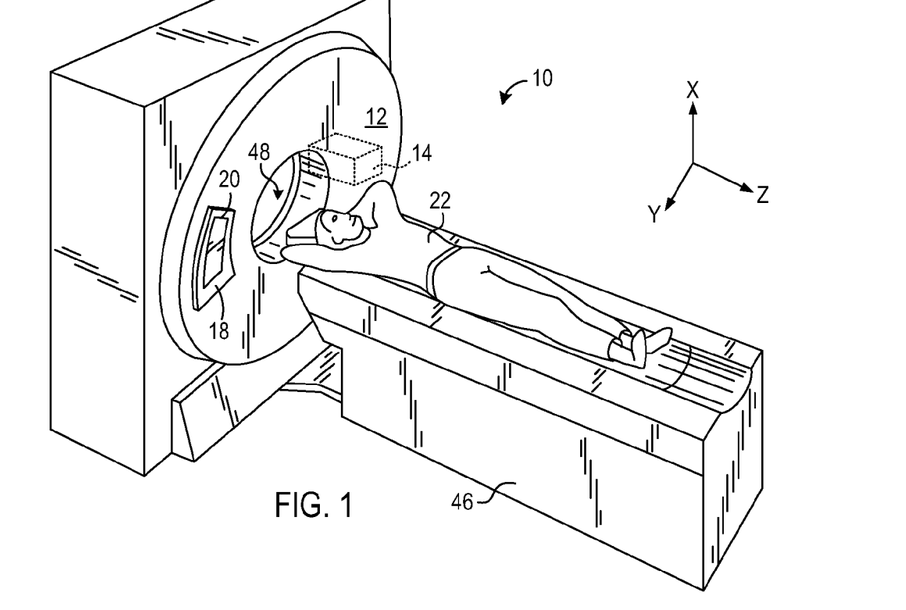
FIG. 1 is a pictorial view of an imaging system.

FIG. 1 is a block diagram of an embodiment of an imaging system 10 designed both to acquire original image data and to process the image data for display and/or analysis in accordance with the present invention. It will be appreciated by those skilled in the art that the present invention is applicable to numerous medical imaging systems implementing an x-ray tube, such as x-ray or mammography systems. Other imaging systems such as computed tomography systems and digital radiography systems, which acquire image three dimensional data for a volume, also benefit from the present invention. The following discussion of x-ray system 10 is merely an example of one such implementation and is not intended to be limiting in terms of modality.

Figure 2:
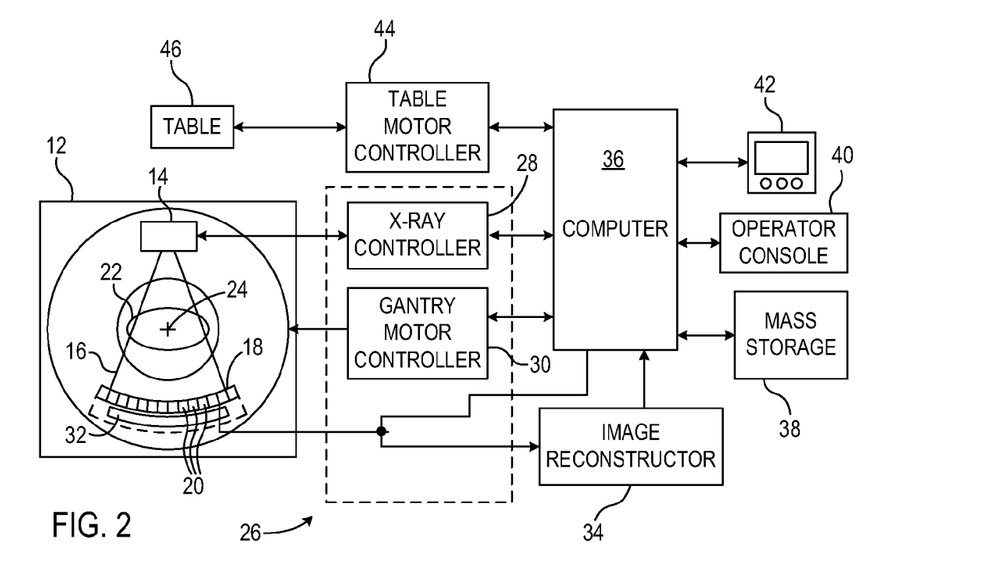
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source assembly 14 that projects a cone beam of x-rays toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source assembly 14 are governed by a control mechanism 26 of CT system 10. Control mechanism 26 includes an x-ray controller 28 that provides power and timing signals to an x-ray source assembly 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patient 22 through a gantry opening 48 of FIG. 1 in whole or in part.

Figure 3:
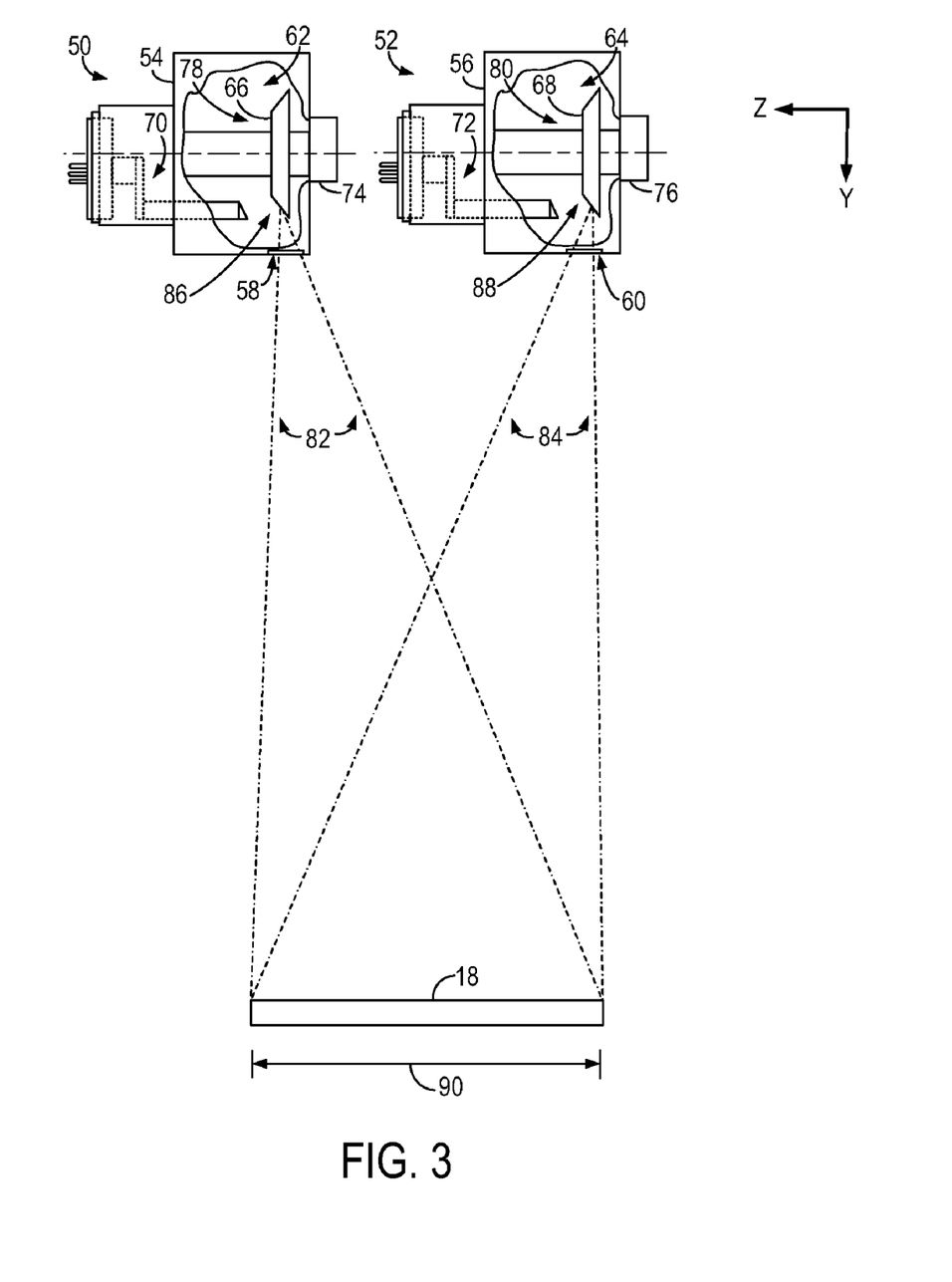
FIG. 3 is a top view of an x-ray tube assembly according to an embodiment of the invention and useable with the system illustrated in FIG. 1.

FIG. 3 illustrates a top view diagram of a portion of imaging system 10 along the x-direction according to an embodiment of the invention. X-ray tube assembly 14 includes a first cone beam x-ray source or x-ray tube 50 and a second cone beam x-ray source or x-ray tube 52, which is offset from first x-ray tube 50 by a distance in the z-direction. Each x-ray tube 50, 52 respectively includes a vacuum chamber or frame 54, 56 having a radiation emission passage 58, 60 formed therein. Each frame 54, 56 respectively encloses a vacuum 62, 64 and houses an anode 66, 68, a cathode assembly 70, 72, and a rotor 74, 76. Each anode 66, 68 includes a respective target face 78, 80.

First and second streams or beams of x-rays 82, 84 emitted from respective x-ray tubes 50, 52 are produced when high-speed electrons are decelerated when directed from cathode assemblies 70, 72 to respective targets 78-80 via a potential difference therebetween of, for example, 60 thousand volts or more in the case of CT applications. For example, when electrons impact target 78 of first x-ray tube 50 at a focal point 86 thereof, first stream of x-rays 82 emits therefrom. In a similar manner, when electrons impact target face 80 of second x-ray tube 52 at a focal point 88 thereof, second stream of x-rays 84 emits therefrom. First stream of x-rays 82 and second stream of x-rays 84 emit through a respective radiation emission passages 58, 60 and fan out toward detector array 18. As shown in FIG. 3, x-ray streams 82, 84 are cast onto the same sensing surface of detector array 18 such that they span a length 90 thereof.

Data acquired from x-ray beams 82, 84 contain information for each row of detector array 18. On the extreme ends of detector array 18 in the z-axis, the effective cone angle for the collected data from one of x-ray tubes 50, 52 is smaller than the effective cone angle for the other x-ray tube 52, 50. The data with the smallest cone angle and correspondingly with the smallest amount of missing data and frequencies can be preferentially weighted during the reconstruction process. At the center of detector array 18 in the z-axis, the data samples collected from each x-ray tube 50, 52 involve effectively the largest cone angle of x-ray beams 82, 84. These data sets can then be utilized with nominal weighting to reduce the amount of missing data and frequencies to produce images.

Figure 4:
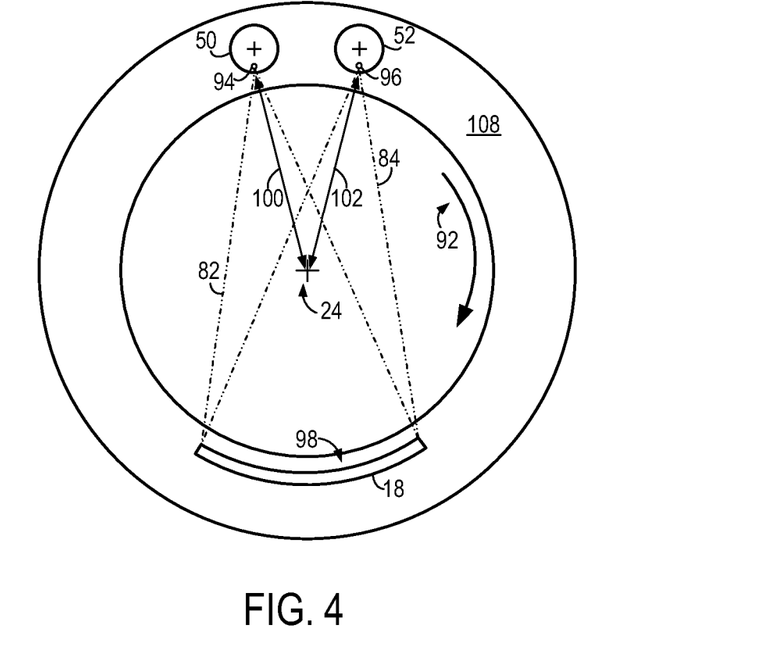
FIG. 4 is a side view diagram of the x-ray tube assembly of FIG. 3.

Referring now to FIG. 4, a side view diagram of x-ray tube assembly 14 is shown with respect to a circumferential direction or a direction of rotation 92 about center of rotation 24. First x-ray tube 50 and second x-ray tube 52 are configured to emit streams of electrons toward respective focal spots 94, 96 such that first and second streams of x-rays 82, 84 cover a surface 98 of detector array 18. As illustrated, second x-ray tube 52 is offset from first x-ray tube 50 by a distance in circumferential direction 92. Also, first x-ray tube 50 is positioned at a first distance 100 from center of rotation 24 and second x-ray tube 52 is positioned at a second distance 102 from center of rotation 24. According to one embodiment, first distance 100 and second distance 102 are of equal length or of substantially equal length. However, one skilled in the art will recognize that first and second x-ray tubes 50, 52 may be configured such that first and second streams of x-rays 82, 84 cover surface 98 of detector 18 while first distance 100 and second distance 102 differ in length.

Figure 5:
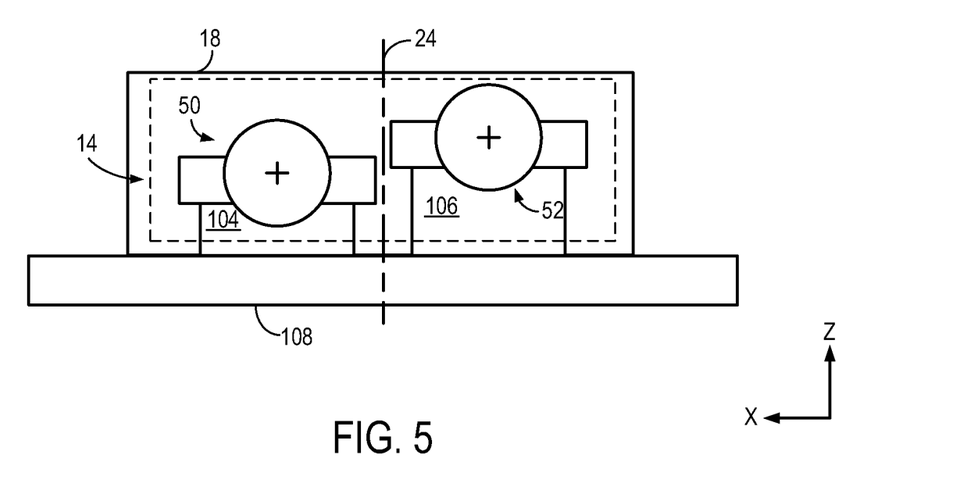
FIG. 5 is a side view diagram of the x-ray tube assembly of FIG. 3.

FIG. 5 shows a side view diagram of another portion of imaging system 10 along the y-direction according to an embodiment of the invention. As illustrated, a combination of the offsets of first and second x-ray tubes 50, 52 in the x- and z-directions is shown. Respective mounting structures 104, 106 secure first and second x-ray tubes 50, 52 in position. Mounting structures 104, 106 are coupled to a rotating base 108, which rotates about center of rotation 24.

In operation, a computer, such as computer 36 of FIG. 2, selectively grids first stream of x-rays 82 and second stream of x-rays 84 such that two sets of image data are acquired during one 360 degree rotation of the gantry—one set of image data corresponding to first stream of x-rays 82 and a second set of image data corresponding to second stream of x-rays 84.

Further, according to one embodiment, first and second x-ray tubes 50, 52 operated at differing energy levels for dual kVp imaging. For example, a computer, such as computer 36 of FIG. 2, may cause first x-ray tube 50 to generate a stream of x-rays having a first energy characteristic, such as, for example 140 kV, and may cause second x-ray tube 52 to generate a stream of x-rays having a second energy characteristic, such as, for example, 80 kV.

When operated sequentially, first and second x-ray tubes 50, 52 emit overlapping fan-shaped streams of x-rays 82, 84 toward detector array 18. The overlap in streams of x-rays 82, 84 increases image data acquisition at edges of fan-shaped streams 82, 84, thereby reducing artifacts generated by data insufficiency in the cone beam geometry.

Figure 6:
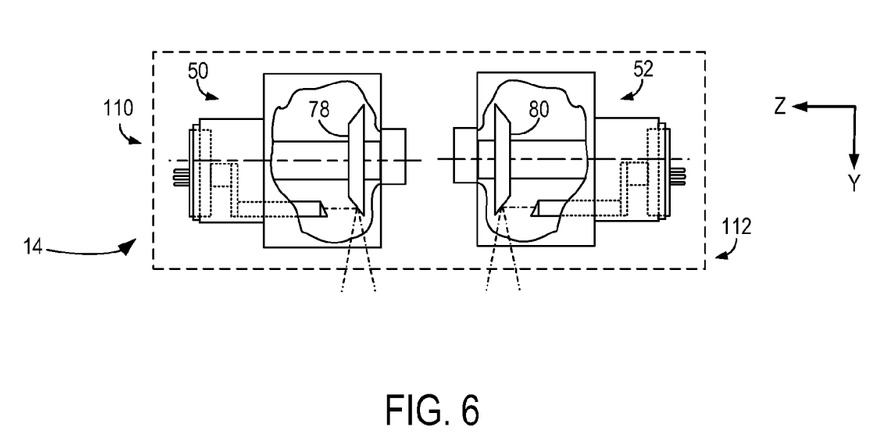
FIG. 6 is a top view diagram of an x-ray tube assembly according to an embodiment of the invention.
Figure 7:
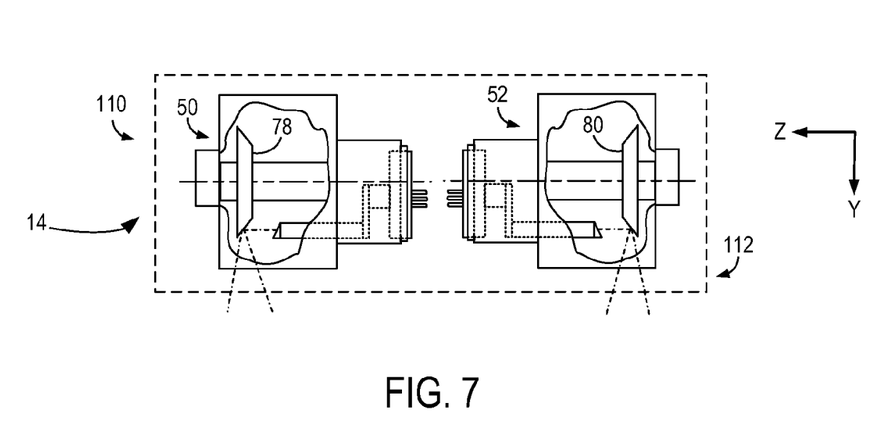
FIG. 7 is a top view diagram of an x-ray tube assembly according to an embodiment of the invention.

Referring back to FIG. 3, according to an embodiment of the invention, first and second x-ray tubes 50, 52 are arranged such that target face 78 of anode 66 of first x-ray tube 50 is facing in a same direction as target face 80 of anode 68 of second x-ray tube 52, such as a positive z-direction as shown in FIG. 3. However, x-ray tubes may be positioned in alternative arrangements, according to other embodiments of the invention. For example, as shown in FIG. 6, first x-ray tube 50 and second x-ray tube 52 may be arranged such that target face 78 faces a first side 110 of x-ray tube assembly 14 and target face 80 faces a second side 112 of x-ray tube assembly 14, with target face 78 of first x-ray tube 50 is facing away from target face 80 of second x-ray tube 52. Alternatively, as shown in FIG. 7, first and second x-ray tubes 50, 52 may be arranged such that target face 78 of first x-ray tube 50 faces second side 112 of x-ray tube assembly 14 and target face 80 of second x-ray tube 52 faces first side 110 of x-ray tube assembly 14. In this arrangement, target faces 80, 82 face each other.

Figure 8:
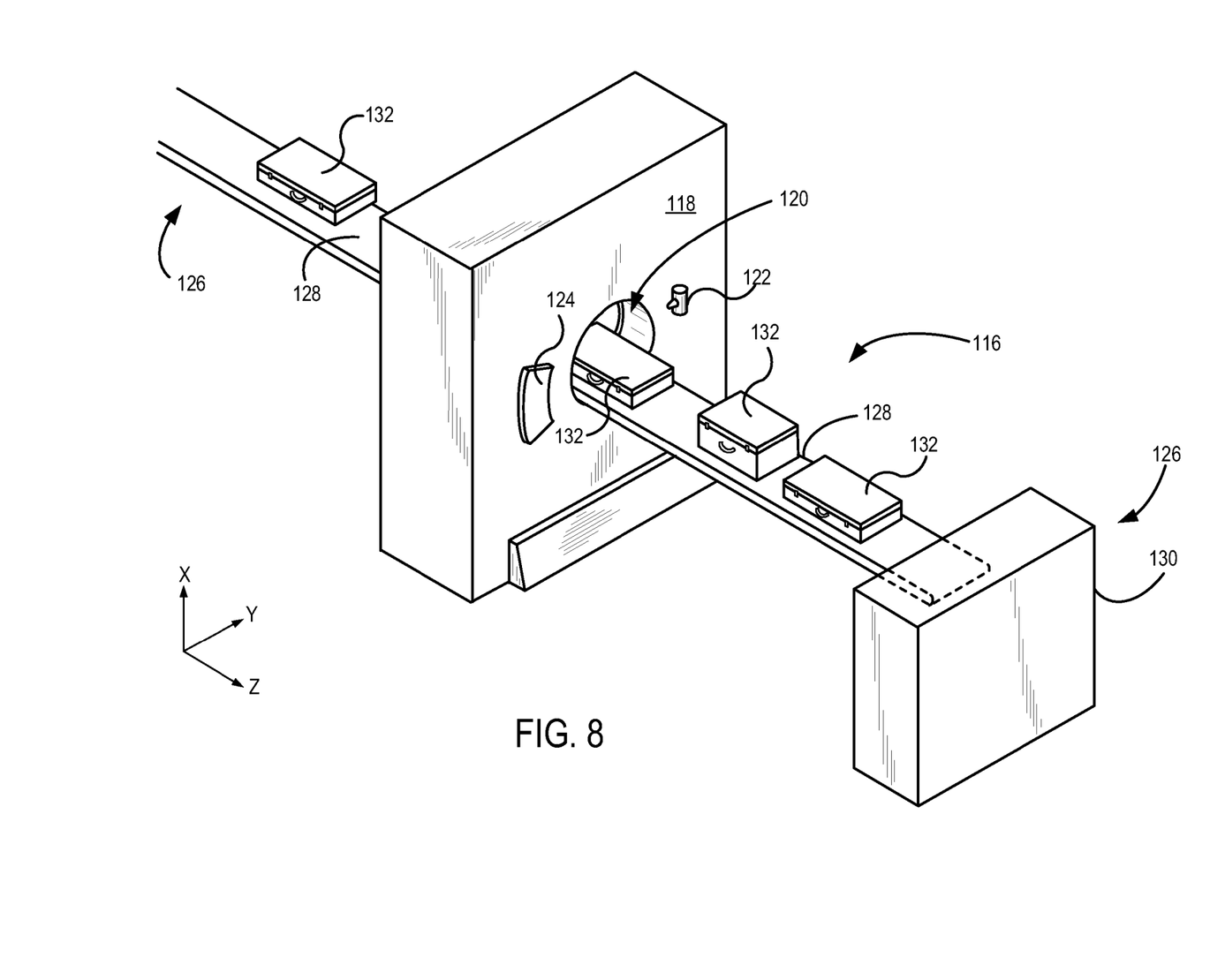
FIG. 8 is a pictorial view of an x-ray system for use with a non-invasive package inspection system.

FIG. 8 is a pictorial view of an x-ray system 116 for use with a non-invasive package inspection system. X-ray system 116 includes a gantry 118 having an opening 120 therein through which packages or pieces of baggage may pass. Gantry 118 houses a high frequency electromagnetic energy source, such as an x-ray tube 122, and a detector assembly 124. A conveyor system 126 is also provided and includes a conveyor belt 128 supported by structure 130 to automatically and continuously pass packages or baggage pieces 132 through opening 120 to be scanned. Objects 132 are fed through opening 120 by conveyor belt 128, imaging data is then acquired, and the conveyor belt 128 removes the packages 132 from opening 120 in a controlled and continuous manner. As a result, postal inspectors, baggage handlers, and other security personnel may non-invasively inspect the contents of packages 132 for explosives, knives, guns, contraband, etc. One skilled in the art will recognize that gantry 118 may be stationary or rotatable. In the case of a rotatable gantry 118, system 116 may be configured to operate as a CT system for baggage scanning or other industrial or medical applications.

According to an embodiment of the invention, an imaging system includes a rotatable gantry having an opening therein to receive a subject to be scanned and configured to rotate about a central axis in a rotation direction. The imaging system also includes a first x-ray source coupled to the rotatable gantry at a first position, wherein the first position is offset from the central axis of the rotatable gantry by a first distance. Further, the imaging system includes a second x-ray source coupled to the rotatable gantry at a second position, wherein the second position is offset from the central axis of the rotatable gantry by a second distance, wherein the second position is offset from the first position in a direction coincident with the rotation direction, and wherein the second position is offset from the first position in a direction parallel to the central axis.

In accordance with another embodiment of the invention, a method of manufacturing an assembly includes coupling a first x-ray tube to a rotatable gantry at a first location, wherein the first location is offset from a center of rotation of the rotatable gantry by a first distance. The method also includes coupling a second x-ray tube to the rotatable gantry at a second location, wherein the second location is offset from the center of rotation of the rotatable gantry by a second distance, offset from the first location in a direction parallel to the center of rotation of the rotatable gantry, and offset from the first location in a direction of rotation of the rotatable gantry.

According to yet another embodiment of the invention, a computed tomography (CT) system includes a gantry having an opening therein for receiving an object to be scanned, the gantry rotatable in a circumferential direction. The CT system also includes a table positioned within the opening of the rotatable gantry and moveable through the opening in a z-direction and a first x-ray tube coupled to the rotatable gantry and configured to emit a first stream of electrons, the first x-ray tube having a first focal spot configured to direct a first beam of x-rays toward a detector. The CT system further includes a second x-ray tube configured to emit a second stream of electrons and having a second focal spot configured to direct a second beam of x-ray beam toward the detector, wherein the second focal spot is offset from the first focal spot by a distance in the z-direction and by a distance in the circumferential direction.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An imaging system comprising:
   a rotatable gantry having an opening therein to receive a subject to be scanned and configured to rotate about a central axis in a rotation direction;
   a first x-ray source coupled to the rotatable gantry at a first position, wherein the first position is offset from the central axis of the rotatable gantry by a first distance;
   a second x-ray source coupled to the rotatable gantry at a second position, wherein the second position is offset from the central axis of the rotatable gantry by a second distance, offset from the first position in a direction coincident with the rotation direction, and offset from the first position in a direction parallel to the central axis;
   a first rotor coupled to the first x-ray source;
   a second rotor coupled to the second x-ray source, wherein the second rotor is constructed to rotate independently of the first rotor;
   a detector array comprising a plurality of detectors coupled to the rotatable gantry; and a computer programmed to:
  cause the first x-ray source to project a first fan beam of x-rays toward the detector array;
  cause the second x-ray source to project a second fan beam of x-rays toward the detector array;
  collect a first set of image data corresponding to x-rays of the first fan beam;
  collect a second set of image data corresponding to x-rays of the second fan beam;
  identify a first effective cone angle of the first fan beam of x-rays corresponding to a given detector of the plurality of detectors;
  identify a second effective cone angle of the second fan beam of x-rays corresponding to the given detector of the plurality of detectors;
  compare the first and second effective cone angles;
  if the first effective cone angle is less than the second effective cone angle, preferentially weight image data of the first set of image data corresponding to the given detector during image reconstruction; and
  if the second effective cone angle is less than the first effective cone angle, preferentially weight image data of the second set of image data corresponding to the given detector during image reconstruction.

2. The imaging system of claim 1 wherein the detector array has a length defined between a first end of the detector array and a second end of the detector array;
  wherein an effective cone angle of the first fan beam of x-rays is greater than an effective cone angle of the second fan beam at the first end of the detector array; and
  wherein an effective cone angle of the second fan beam of x-rays is greater than an effective cone angle of the first fan beam at the second end of the detector array.

3. The imaging system of claim 1 wherein the computer is further programmed to:
  nominally weight the image data of first and second sets of image data corresponding to the given detector if the first and second effective cone angles are approximately equal.

4. The imaging system of claim 1 wherein the first distance is substantially equal to the second distance.

5. The imaging system of claim 1 wherein the computer is further programmed to:
  selectively grid the first fan beam of x-rays to collect the first set of image data in a single rotation of the gantry; and
  selectively grid the second fan beam of x-rays to collect the second set of image data in the single rotation of the gantry.

6. The imaging system of claim 5 wherein the gantry rotates approximately 360 degrees during the single rotation of the gantry.

7. The imaging system of claim 1 wherein the computer is further programmed to:
  cause the first x-ray source to project the first fan beam of x-rays corresponding to a first energy characteristic; and
  cause the second x-ray source to project the second fan beam of x-rays corresponding to a second energy characteristic.

8. The imaging system of claim 1 wherein the first x-ray source comprises a first anode having a first target face configured to face in a first direction; and
  wherein the second x-ray source comprises a second anode having a second target face configured to face in a second direction opposite to the first direction.

9. The imaging system of claim 1 wherein the first x-ray source comprises a first anode having a first target face configured to face in a first direction; and
  wherein the second x-ray source comprises a second anode having a second target face configured to face in the first direction.

10. A method of manufacturing an assembly comprising:
  coupling a first x-ray tube to a rotatable gantry at a first location, wherein the first location is offset from a center of rotation of the rotatable gantry by a first distance;
  coupling a second x-ray tube to the rotatable gantry at a second location, wherein the second location is:
    offset from the center of rotation of the rotatable gantry by a second distance;
    offset from the first location in a direction parallel to a central axis of rotation of the rotatable gantry; and
    offset from the first location in a direction of rotation of the rotatable gantry;
  configuring the first x-ray tube to emit a first beam of x-rays at a first energy level toward a detector assembly;
  configuring the second x-ray tube to emit a second beam of x-rays at a second energy level toward the detector assembly; and
  coupling a computer to the detector assembly, wherein the computer is programmed to:
    identify a first set of image data acquired at a detector element of the detector assembly corresponding to the first beam of x-rays;
    identify a second set of image data acquired at the detector element of the detector assembly corresponding to the second beams of x-rays;
    wherein the first and second sets of image data correspond to the same detector element of the detector assembly; and
    selectively weight the first and second sets of image data based on an effective cone angle of the first beam of x-rays for the detector element and based on an effective cone angle of the second beam of x-rays for the detector element.

11. The method of claim 10 further comprising:
  positioning the first x-ray tube such that a target face of an anode of the first x-ray tube faces a first direction; and
  positioning the second x-ray tube such that a target face of an anode of the second x-ray tube faces the first direction.

12. The method of claim 10 further comprising:
  positioning the first x-ray tube such that a target face of an anode of the first x-ray tube faces a first direction; and
  positioning the second x-ray tube such that a target face of an anode of the second x-ray tube faces a second direction opposite to the first direction.

13. A computed tomography (CT) system comprising:
  a gantry having an opening therein for receiving an object to be scanned, the gantry rotatable in a circumferential direction;
  a table positioned within the opening of the rotatable gantry and moveable through the opening in a z-direction;
  a first x-ray tube coupled to the rotatable gantry and configured to emit a first stream of electrons, the first x-ray tube having a first focal spot configured to direct a first beam of x-rays toward a detector assembly;
  a second x-ray tube configured to emit a second stream of electrons and having a second focal spot configured to direct a second beam of x-ray beam toward the detector assembly, wherein the second focal spot is offset from the first focal spot by a distance in the z-direction and by a distance in the circumferential direction; and a computer programmed to:
cause the first x-ray tube to direct the first beam of x-rays toward the object;
cause the second x-ray tube to direct the second beam of x-rays toward the object;
identify image data acquired by a sub-portion of the detector assembly corresponding to the first beam of x-rays;
identify image data acquired by the sub-portion of the detector assembly corresponding to a the second beam of x-rays;
compare an effective cone beam angle of the first beam of x-rays for the sub-portion of the detector assembly with an effective cone beam angle of the second beam of x-rays for the sub-portion of the detector assembly; and
reconstruct an image of the object using image data acquired by the sub-portion of the detector assembly, wherein reconstruction of the image comprises preferentially weighting the image data corresponding to one of the first beam of x-rays and the second beam of x-rays based on the comparison of the effective cone beam angles of the first and second beam of x-rays.

14. The CT system of claim 13 wherein reconstruction of the image comprises at least one of:
nominally weighting image data identified as corresponding to maximum effective cone beams angles of the first and second beams of x-rays; and
preferentially weighting image data identified as corresponding to minimum effective cone beam angles of the first and second beams of x-rays.

15. The CT system of claim 13 wherein the computer is further programmed to:
cause the first x-ray tube to emit the first beam of x-rays at a first energy level; and
cause the second x-ray tube to emit the second beam of x-rays at a second energy level.

16. The CT system of claim 15 wherein the computer, in being programmed to collect image data, is programmed to collect dual-energy image data.

17. The CT system of claim 13 wherein the computer is further programmed to selectively grid the first and second beams of x-rays.

18. The CT system of claim 17 wherein the computer is further programmed to:
collect a first set of image data in a single rotation of the gantry and corresponding to the first beam of x-rays; and
collect a second set of image data in the single rotation of the gantry and corresponding to the second beam of x-rays.

19. The CT system of claim 13 wherein the first focal spot is positioned on a first anode configured to face in a first direction; and
wherein the second focal spot is positioned on a second anode configured to face in a second direction opposite to the first direction.

20. The CT system of claim 13 wherein the first focal spot is positioned on a first anode configured to face in a first direction; and
wherein the second focal spot is positioned on a second anode configured to face in the first direction.

* * * * *